US00PP34191P2

(12) United States Plant Patent
Coetzee

(10) Patent No.: US PP34,191 P2
(45) Date of Patent: May 3, 2022

(54) GRAPEVINE PLANT NAMED 'NAVSEL 21'

(50) Latin Name: *Vitis vinifera*
Varietal Denomination: NAVSEL 21

(71) Applicant: Special New Fruit Licensing Limited, Peterborough (GB)

(72) Inventor: Gideon Jacobus Nicolaas Coetzee, Peterborough (GB)

(73) Assignee: Special New Fruit Licensing Limited, Peterborough (GB)

( * ) Notice: Subject to any disclaimer, the term of this patent is extended or adjusted under 35 U.S.C. 154(b) by 0 days.

(21) Appl. No.: 17/117,451

(22) Filed: Dec. 10, 2020

(51) Int. Cl.
*A01H 6/88* (2018.01)
*A01H 5/08* (2018.01)

(52) U.S. Cl.
USPC ..... Plt./216

(58) Field of Classification Search
USPC ..... Plt./216
See application file for complete search history.

(56) References Cited

U.S. PATENT DOCUMENTS

PP23,125 P2 10/2012 Sheehan

OTHER PUBLICATIONS

U.S. Appl. No. 17/117,438, filed Dec. 10, 2020, Coetzee.

*Primary Examiner* — Annette H Para
(74) *Attorney, Agent, or Firm* — Dentons US LLP

(57) ABSTRACT

'NAVSEL 21' is a new and distinct grapevine plant with novel characteristics that include naturally tight bunches and red seedless berries. The berries produced by 'NAVSEL 21' have a very firm texture and no detectable seed traces, with a prominent muscat flavour. The berries produced by 'NAVSEL 21' are large, weighing 10 g/berry on average, and are harvested in July in Murcia Region in Spain.

1 Drawing Sheet

Latin name of the genus and species of the plant claimed: *Vitis vinifera.*

Cultivar denomination: 'NAVSEL 21'.

BACKGROUND OF THE INVENTION

The present invention relates to a new distinct variety of seedless grapevine named 'NAVSEL 21'. The variety originated from a hybridization performed in Wellington, South Africa in 2010 between 'Sheegene 20' (U.S. Plant Pat. No. 23,125P2), as the seed parent, and '9-762' (unpatented), as the pollen parent. Abortive seed traces were embryo cultured and the resulting plant was planted in an evaluation block during 2011. The first evaluation of the fruit produced by 'NAVSEL 21' was performed during 2013. 'NAVSEL 21' was first asexually propagated by field grafting dormant hardwood scions to rootstock in 2014 in South Africa. Fruit from the resulting four grafted 'NAVSEL 21' vines was first harvested in 2016. All characteristics and distinctions remain true to form and are established and transmitted through succeeding propagations.

SUMMARY OF THE INVENTION

The following are the most outstanding and distinguishing characteristics of 'NAVSEL 21'. 'NAVSEL 21' produces large, red (5R 3/4), seedless berries that are harvested in late July, in Spain (Murcia Region) and weigh on average 10 g/berry.

The new cultivar is distinguished from its male parent '9-762' in that NAVSEL 21 produces red-coloured grapes while '9-762' produces green coloured grapes. NAVSEL 21 berry shape is cylindrical compared to the ellipsoidal berry shape of '9-762'.

'NAVSEL 21' is believed to be most similar to 'Sheegene 20'. Nonetheless, the new cultivar is distinguished from its female parent, 'Sheegene 20' in that NAVSEL 21 produces berries with prominent muscat flavour whereas 'Sheegene 20' produces berries having a neutral flavour.

Additionally, 'NAVSEL 21' is an early season cultivar harvested in July, in the Murcia region in Spain, which is distinguishable from both the August harvest period of '9-762' and the September harvest period of 'Sheegene 20'.

Similar to 'NAVSEL 21,' 'NAVSEL 20' (U.S. patent application Ser. No. 17/117,438) is another grapevine variety that is an early season cultivar harvested in July. Nonetheless, plants of 'NAVSEL 21' and 'NAVSEL 20' can be readily and unambiguously distinguished from one another at least based upon their plant habit and growth, skin color, trunk characteristics, time of bud burst, and floral clusters. For example, 'NAVSEL 21' exhibits a horizontal growth habit, thicker trunk, 5R 3/4 skin color, earlier bud burst, and increased inflorescences per cluster, whereas 'NAVSEL 20' exhibits a semi-erect growth habit, thinner trunk; 5RP 3/2 skin color, later bud burst, and fewer inflorescences per cluster.

BRIEF DESCRIPTION OF THE DRAWING

FIG. 1 Shows the form, foliage, and fruit of a 4-year-old 'NAVSEL 21' vine grown in the field in Murcia, Spain. The colors shown are as true as can be reasonably obtained by conventional photographic procedures.

DETAILED BOTANICAL DESCRIPTION

The following detailed description sets forth the distinctive characteristics of 'NAVSEL 21'. The detailed description was obtained between March and November using 4-year-old plants grown in the field in Murcia, Spain. The color references are to the *Munsell Plant Tissue Color Book,* 2012 Edition by Munsell Color.

Classification:

*Family*.—Vitaceae.

*Botanical.—Vitis vinifera.*

*Common name*.—Grapevine.

*Cultivar name*.—'NAVSEL 21'.

Plant:

*Plant habit and growth*.—Horizontal.

*Age at maturity*.—4 years old.

*Size* (*at maturity*).—Height: 225 cm. Width: 300 cm.

*Vigor*.—Medium to high.

*Productivity*.—Medium.

*Rootstock*.—Name of rootstock: 1103 Paulsen Rootstock. Age of rootstock at time of grafting: one year old.

Trunk:

*Size*.—Diameter: 7.5 cm.

*Surface texture*.—Smooth.

*Bark color*.—Exterior: 5 YR 5/2. Interior: 5 YR 4/4.

Canes:

*Size*.—Diameter: 12 mm. Length: 200 cm.

*Surface texture*.—Mature cane: smooth. Immature cane: smooth and very slightly ribbed Form (woody shoot cross section form): pith in center with diaphragm at the nodes.

*Color*.—Mature: 5 GY 5/6 at 5 months (anthocians: 5R 3/6). Immature: 2.5GY 5/8 at 4 weeks (anthocians: 5R 3/4). Dorsal side of internodes: 2.5R 4/6 at 5 months. Ventral side of internodes: 5GY 6/6 at 5 months. Dorsal side of nodes: 2.5R 4/6 at 5 months. Ventral side of nodes: 5GY 6/6 at 5 months.

*Internode length* (*upper mature sun cane*).—19.75 cm (on June 15).

*Internode width*.—7.80 mm (on 15 June).

*Node width*.—14.1 mm (on June 15).

Bud:

*Bud description*.—Winter bud: color 2.5YR 4/4; medium, rounded and pointed. Green bud: color 5GY6/6; no anthocyanin coloration.

*Time of bud burst*.—50% bud break by February 26.

*Time of bud leaf burst.—March* 2.

Tendrils:

*Form*.—Mostly bifid and trifid.

*Size*.—Medium.

*Length*.—22 cm.

*Diameter*.—1.75 mm.

*Texture and distribution of tendril at each node beginning at base*.—Smooth and discontinuous; 0000011011110110101 (0 means no tendril at that node and 1 means there is tendril at the node).

*Color*.—Mature: 2.5GY 6/8 at 4 weeks. Immature: 5Y 5/4 at 10 days.

*Anthocyanin*.—Mature: 10 R 3/4. Immature: 5 YR 4/4.

Growing tips (young shoot):

*Pubescence*.—Absent.

*Color*.—5 GY 4/6.

*Anthocyanin*.—Present, 10 R 3/2.

*Shape*.—Fully open.

*Apex*.—Triangular.

*Form of tip*.—Fully open.

*Shoot attitude before tying*.—Horizontal.

Leaves:

*Shape*.—Pentagonal.

*Density*.—Medium.

*Apex*.—Pointed.

*Base*.—Rounded.

*Number of lobes*.—5.

*Depth of upper lateral sinuses of mature leaves*.—Deep.

*Arrangement of lobes of upper lateral sinuses on mature leaves*.—Strongly overlapped.

*Margin*.—Irregular teeth.

*Length of teeth on margin*.—2-10 mm.

*Shape of teeth on margin*.—Both sides convex.

*Texture* (*mature leaf*).—Upper surface: slightly bullated along veins, otherwise smooth. Lower surface: glabrous, smooth.

*Size*.—Immature: Length: 8 cm at 10 days. Width: 8 cm at 10 days. Mature: Length: 18.2 cm at 4 weeks. Width: 19.5 cm at 4 weeks.

*Color*.—Immature leaf: Upper surface: 2.5 GY 5/6; anthocyanin 2.5 YR 3/6. Lower surface: 5 GY 5/6; anthocyanin 2.5 YR 4/6. Mature leaf: Upper surface: 5 GY 4/4. Lower surface: 5GY 5/4.

*Venation*.—Pattern: veins on upper leaf are flat; veins on lower leaf are raised. Length of middle vein in mature leaves: 11.65 cm. Color: Upper surface: 5 Y 5/4. Lower surface: 2.5 GY 6/4.

*Petiolar sinus include general description half open.—*

*Petiole*.—Length: 13.6 cm. Diameter: 3.2 mm. Color: 2.5GY 5/6.

Floral cluster:

*General description and location*.—Mostly $4^{th}$ node; 20% without shoulders.

*Quantity of inflorescences per cluster*.—940.

*Size*.—Length: 24.125 cm. Width: 20 cm (spread); 12.25 cm (hanging).

*Peduncle length*.—5.5 cm.

*Inflorescences*.—Hermaphroditic.

*Stamens*.—Straight, 3 mm.

*Anthers*.—Small and nondescript.

*Date of bloom*.—Start of bloom, April 23; and 100% bloom, May 6.

*Pollen amount*.—Sparse.

*Calyptra*.—5 segments with complete separation.

*Calyptra color*.—5GY 4/8.

Fruit:

*Time of year of commercial harvest and shipment*.—Early season, end of July.

*Keeping quality*.—Good condition overall. After 30 days of storage, the variety might show slight symptoms of dehydration of the pedicel. Good eating quality after 30 days, the berries keep the muscat flavor and crunchy texture.

*Cluster* (*primary bunches*).—General size: medium (550 g tipped and 600 g not tipped). Length (without peduncle): 22.8 cm tipped and 27 cm not tipped. Width: 12 cm (hanging), 16.2 cm (spread). Density: tight. Peduncle: Length: 7.4 cm. Diameter: 5.6 mm. Color: 2.5GY 6/6. Number of berries per cluster: 62 tipped and 70 not tipped. Berry: Size: large (11 g). Diameter: 22 mm. Length: 28 mm. Shape: mostly cylindrical. Uniformity: some variability. Brix content: 17° Brix. Skin color: 5R 3/4. Pedicel: Length: 11.6 mm. Diameter: 2.3 mm. Color: 2.5 GY 7/6. Strength of attachment to berry: strong.

*Cluster* (*secondary bunches*).—General size: medium (154 g). Length (without peduncle): 11.7 cm. Width: 8.4 cm (hanging), 12.2 cm (spread). Density: tight. Peduncle: Length: 5.8 cm. Diameter: 3.4 mm. Color: 2.5 GY 7/6. Number of berries per cluster: 24. Berry: Size: large (6.5 g). Diameter: 20.3 mm. Length: 25.8 mm. Shape: mostly cylindrical. Uniformity: some variability. Brix content: 19.1° Brix. Titratable acidity: 0.55%. Color: Skin color (mature berry) without bloom: 5R 3/4. Skin color (mature berry) with bloom: 5R 3/4. Color of immature berry skin with bloom: 5R 4/6. Color of immature berry skin without bloom: 5R 4/6. Pedicel: Length: 2.41 mm. Diameter: 9 mm. Color: 2.5GY 6/6. Strength of attachment to berry: strong.

Berry flesh:

*Color*.—2.5GY 8/4.

*Juice color*.—Clear 2.5 GY 8/4.

*Juice production*.—Medium, 22% wt/wt.

*Thickness of skin*.—Medium.

*Flavor*.—Light muscat.

*Fragrance*.—Neutral.

*Texture*.—Firm.

*Seeds*.—Seed rudiments not detectable.

*Use*.—Fresh table.

Disease and insect resistance: The disease and insect resistance of this cultivar is typical of its species.

What is claimed is:

1. A new and distinct variety of grapevine named 'NAVSEL 21' as shown and described herein.

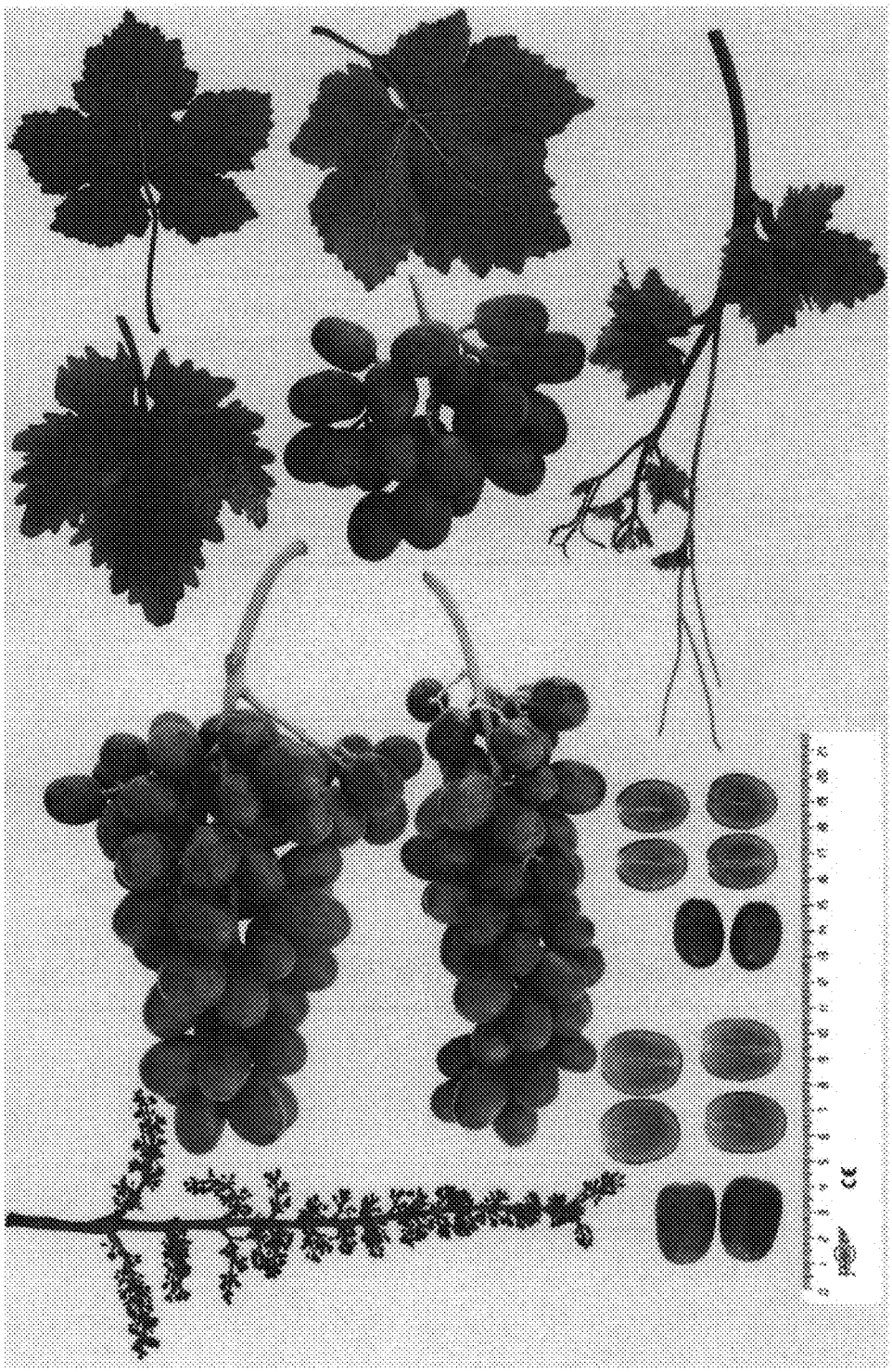

* * * * *